US00PP09273P

United States Patent [19]

Olesen et al.

[11] Patent Number: Plant 9,273

[45] Date of Patent: Sep. 5, 1995

[54] MINIATURE ROSE PLANT NAMED 'POULLEN'

[75] Inventors: Pernille Olesen; Mogens N. Olesen, both of Fredensborg, Denmark

[73] Assignee: DeVor Nurseries, Inc., Watsonville, Calif.

[21] Appl. No.: 310,712

[22] Filed: Sep. 21, 1994

[51] Int. Cl.[6] ..... A01H 5/00

[52] U.S. Cl. ..... Plt./9

[58] Field of Search ..... Plt. 1, 9, 26

*Primary Examiner*—Howard J. Locker

*Attorney, Agent, or Firm*—Christie, Parker & Hale

[57] ABSTRACT

A new low growing miniature rose plant producing small, double, soft pink flowers.

1 Drawing Sheet

SUMMARY OF THE INVENTION

The present invention relates to a new and distinct variety of rose plant of the miniature rose class, which was originated by my crossing as seed and pollen parents two unnamed, unpatented and proprietary seedlings of our creation. The varietal denomination of this new rose is 'Poullen'.

Among the novel characteristics possessed by this new variety which distinguishes it from its parents and all other varieties of which I am aware are its low growing, very compact plants which produce small, double, soft pink flowers in abundance.

Asexual reproduction by budding of the new variety, as performed in Watsonville, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character. Phenotypic expression may vary with light, environmental and cultural conditions.

DESCRIPTION OF THE NEW VARIETY

The following is a detailed description of my new variety, with color terminology in accordance with The Royal Horticultural Society Color Chart (RHSCC). The terminology used in color description herein refers to plate numbers in the aforementioned color chart. Where general terms such as average, normal, medium, ordinary, etc. are used, the characteristics so described are not considered distinguishing.

Parentage: Seedling.

*Seed parent.*—Unnamed seedling.

*Pollen parent.*—Unnamed seedling.

Class: Miniature.

The following observations are made of specimens grown under glass in Watsonville, Calif., in the month of May.

FLOWER

Bloom habit: Recurrent in Watsonville, Calif. from April to December.

A. Bud:

(1) *Size.*—Small.

(2) *Form.*—Pointed, slightly tapering.

(3) *Color.*—When sepals first divide, bud coloration is near 52D with near 52D in center.

(4) *Sepals.*—Longer than bud, foliated near 146A, some small leaf-like appendages may protrude from some sepals.

(5) *Peduncle.*—Length: About 3 to 5 cm. Aspect: Near straight, smooth. Strength: Erect, slender. Color: Near 146A.

(6) *Bracts.*—Occasional, 1 to 2 cm below bud, near 147A.

B. Bloom:

(1) *Size.*—Average size when fully expanded — about 3 cm.

(2) *Borne.*—Sprays of as many as 15 to 20 flowers.

(3) *Form.*—Somewhat pointed at first, becoming flat; fully open bloom shows orange pollen.

(4) *Petalage.*—Under normal conditions average is about 33 to 37.

(5) *Color* (*⅓ to ½ open*).—Outer petals — Top surface near 56B. Undersurface near 55C. Inner petals — Top surface near 56C. Undersurface near 56B. Base of petals (point of attachment) near 7A. General tonality from a distance — pink.

(6) *Color* (*Fully open*).—Outer petals — Top surface near 55D. Undersurface near 55C. Inner petals — Top surface near 56B. Undersurface near 55C. Base of petals (point of attachment) near 7A. General tonality from a distance — pink.

(7) *Color change.*—Color lightens to a softer, paler pink, Petal top surface pink, Petal undersurface pink. General tonality at a distance — pink.

(8) *Lasting quality.*—Long lasting on the plant but does not last well after cutting.

C. Petals:

(1) *Texture.*—Average, thick, smooth.

(2) *Appearance.*—Inside smooth and semi-velvety and outside is smooth but more matte.

(3) *Form.*—Ovoid to fan shaped.

(4) *Arrangement.*—Regularly arranged, imbricated but becomes informal in fully open bloom.

(5) *Petaloids in center.*—Few.
(6) *Persistence.*—Petals drop off cleanly.
(7) *Fragrance.*—Mild fruity fragrance.

REPRODUCTIVE ORGANS

A. Stamens, filaments and anthers:
*Arrangement and color.*—Regularly arranged around styles; stamens near 13A, anthers near 22A; filaments near 145C.
B. Pollens:
*Color.*—Near 22A.
C. Styles: Medium length, bunched even.
D. Stigmas:
*Color.*—Near 13D.
E. Hips: None observed.

PLANT

A. Form: Compact, low growing.
B. Growth: Vigorous, free branching.
*Height attained.*—About 65 cm.
C. Foliage: Compound 3, 5 and 7 leaflets.
(1) *Size.*—Small.
(2) *Quality.*—Abundant.
(3) *Color.*—New foliage: Upper side — near 143A. Under side — near 137C. Old foliage — near 147A, 147B.
(4) *Shape.*—Ovate.
(5) *Texture.*—Upper side — semi-glossy, slightly leather. Under side — smooth, slightly leather.
(6) *Edge.*—Serrate.

(7) *Denticulate.*
(8) *Leaf stem.*—Color — medium green.
(9) *Stipules.*—Medium length, slightly bearded.
(10) *Petioles.*—Top — near 147A. Underside — near 146A.
(11) *Rachis.*—Small prickles underneath, smooth on top.
(12) *Auricle.*—Short, slender, tip with glands, face away from flower.
(13) *Resistance to distance.*—Very resistant to mildew, blackspot and rust.
D. Wood:
*New shoots.*—Near 146B.
*Bark.*—Smooth.
*Old wood.*—Near 147B.
*Bark.*—Smooth with some rough spots.
E. Thorns:
*Quality (main stalk).*—Many.
*Form.*—Thin, curved downwardly, small.
*Length.*—Medium.
*Color.*—Near 160B.
*Position.*—Irregular.
*Prickles.*—Many.
Winter hardiness: Winter hardy in Coastal Califorina.

I claim:

1. A new and distinct variety of rose plant of the miniature rose class, substantially as shown and described.

* * * * *

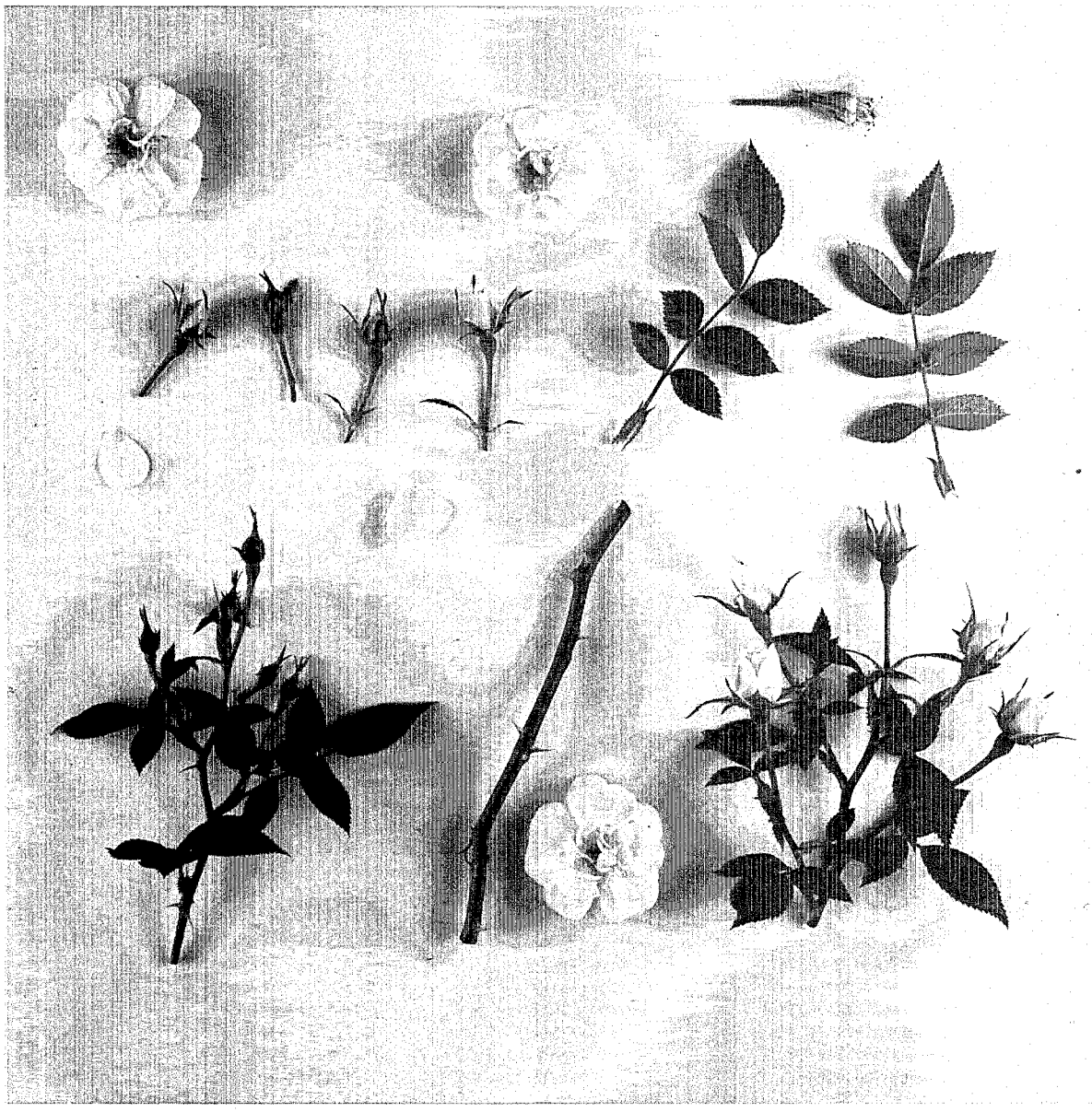

UNITED STATES PATENT AND TRADEMARK OFFICE

CERTIFICATE OF CORRECTION

PATENT NO. : Plant 9,273

DATED : September 5, 1995

INVENTOR(S) : Pernille Olesen; Mogens N. Olesen

It is certified that error appears in the above-indentified patent and that said Letters Patent is hereby corrected as shown below:

Column 2, line 9, before "with" delete "52D" and insert therefor -- 52B --.

Column 3, line 10, change "Pollens" to -- Pollen --.

Column 4, line 1, before "Denticulate" insert -- Serration: --.

Column 4, line 10, delete "distance" and insert therefor -- disease --.

Signed and Sealed this

Sixteenth Day of July, 1996

*Attest:*

Bruce Lehman

BRUCE LEHMAN

*Attesting Officer*

*Commissioner of Patents and Trademarks*